(12) United States Patent
Tang et al.

(10) Patent No.: US 9,018,242 B2
(45) Date of Patent: Apr. 28, 2015

(54) SALT FORM OF TYROSINE KINASE INHIBITOR

(71) Applicant: Jiangsu Simcere Pharmaceutical R&D Co., Ltd, Nanjing (CN)

(72) Inventors: Feng Tang, Nanjing (CN); Qiu Jin, Nanjing (CN); Wei Li, Nanjing (CN); Tian Zhu, Nanjing (CN); Yang Hu, Nanjing (CN); Feng Shao, Nanjing (CN)

(73) Assignee: Jiangsu Simcere Pharmaceutical R&D Co., Ltd, Nanjing (CN)

( * ) Notice: Subject to any disclaimer, the term of this patent is extended or adjusted under 35 U.S.C. 154(b) by 0 days.

(21) Appl. No.: 14/023,486

(22) Filed: Sep. 11, 2013

(65) Prior Publication Data

US 2014/0011856 A1    Jan. 9, 2014

Related U.S. Application Data

(63) Continuation of application No. PCT/CN2012/072174, filed on Mar. 12, 2012.

(30) Foreign Application Priority Data

Mar. 15, 2011  (CN) .......................... 2011 1 0061774

(51) Int. Cl.
*A61K 31/4045* (2006.01)
*C07D 209/42* (2006.01)

(52) U.S. Cl.
CPC .......... *A61K 31/4045* (2013.01); *C07D 209/42* (2013.01)

(58) Field of Classification Search
CPC .......................... C07D 209/42; A61K 31/4045
USPC .......................................... 548/455; 514/414
See application file for complete search history.

(56) References Cited

U.S. PATENT DOCUMENTS 8,084,621 B2 * 12/2011 Tang et al. .................... 548/455

FOREIGN PATENT DOCUMENTS

WO    WO2008/067756 A1 *  6/2008

OTHER PUBLICATIONS

Cancer and Metastasis Reviews (1998), 17(1), 91-106.*
Science (1999), vol. 286, 531-537.*
Cancer [online], [retrieved on Jul. 6, 2007]. Retrieved from the internet, URL http://www.nlm.nih.gov/medlineplus/cancer.html>.*
Cancer [online], [retrieved on Jul. 6, 2007]. Retrieved from the internet, URL; http://en.wikipedia.org|wiki|Cancer.*

* cited by examiner

*Primary Examiner* — Shawquia Jackson
(74) *Attorney, Agent, or Firm* — Syncoda LLC; Feng Ma

(57) ABSTRACT

Provided are acid addition salts of (Z)—N-[2-(diethylamino) ethyl]-2-methyl-7-(1,2-dihydro-5-fluoro-2-oxo-3H-indol-3-ylidene)-4,5,6,7-tetrahydro-1H-indol-3-carboxamide, wherein the salt comprising at least one of a number of salts including L-malate, hydrochloride, phosphate, L-tartrate, benzenesulfonate, sulfate, methanesulfonate, succinate, citrate, fumarate, p-toluenesulfonate, hydrobromate, L-mandelate, lactate, acetate or maleate salt. Also provided is a pharmaceutical composition comprising the salt compounds, and a method of treatment by administering a therapeutically effective amount of the salt compounds as preparation of medicaments.

15 Claims, No Drawings

SALT FORM OF TYROSINE KINASE INHIBITOR

CROSS-REFERENCE TO RELATED APPLICATIONS

The present application is a continuation of PCT/CN2012/072174, filed on Mar. 12, 2012, which claims priority to CN 201110061774.1, filed on Mar. 15, 2011. The disclosures of these applications are hereby incorporated by reference in their entirety.

BACKGROUND

Glivec and Iressa are small-molecule tyrosine kinase inhibitors used in earlier clinical tumor therapy and have good clinical effect, which greatly stimulates interests of global leading pharmaceutical companies and research institutions in the study of such targets. Therefore, researchers have made many efforts in design, synthesis and preclinical studies of a great number of small-molecule inhibitors against many tyrosine kinase targets. Currently, many small-molecule tyrosine kinase inhibitors have been approved for clinical treatment of malignant tumors, while a number of medicaments are under clinical trials, showing broad prospects for development of such tumor-targeted molecular drugs. See, Zhang Shige, Evaluation and Analysis of Drug-Use in Hospitals of China, 2010, 10, 1: 4-6.

The pharmaceutically active compound (Z)—N-[2-(diethylamino)ethyl]-2-methyl-7-(1,2-dihydro-5-fluoro-2-oxo-3H-indol-3-ylidene)-4,5,6,7-tetrahydro-1H-indol-3-carboxamide (represented by Formula I) has significant activity in inhibition of multiple tyrosine kinases, and is capable of inhibiting proliferation of a variety of human cancer cell lines. Therefore, it can be used in preparation of anti-tumor drugs. See, Tang Feng, et al., WO2008/067756 (2008), for detailed description of biological activities of the compound and preparation thereof. The disclosures of WO2008/067756 is hereby incorporated by reference in its entirety.

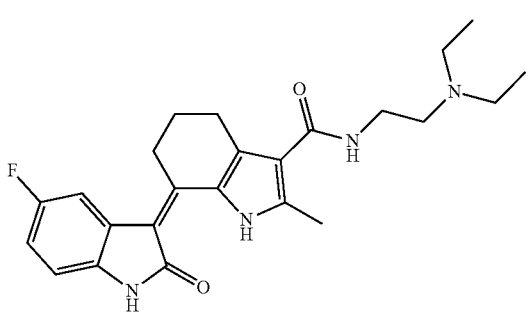

Formula I

SUMMARY

In an aspect, an acid addition salt of (Z)—N-[2-(diethylamino)ethyl]-2-methyl-7-(1,2-dihydro-5-fluoro-2-oxo-3H-indol-3-ylidene)-4,5,6,7-tetrahydro-1H-indol-3-carboxamide is provided.

In some implementations, the salt comprises at least one of L-malate, hydrochloride, phosphate, L-tartrate, benzenesulfonate, sulfate, methanesulfonate, succinate, citrate, fumarate, p-toluenesulfonate, hydrobromate, L-mandelate, lactate, acetate or maleate salt of (Z)—N-[2-(diethylamino)ethyl]-2-methyl-7-(1,2-dihydro-5-fluoro-2-oxo-3H-indol-3-ylidene)-4,5,6,7-tetrahydro-1H-indol-3-carboxamide.

In some implementations, the salt comprises at least one of L-tartrate, benzenesulfonate, L-mandelate, succinate, L-malate, citrate, hydrochloride, phosphate or lactate salt of (Z)—N-[2-(diethylamino)ethyl]-2-methyl-7-(1,2-dihydro-5-fluoro-2-oxo-3H-indol-3-ylidene)-4,5,6,7-tetrahydro-1H-indol-3-carboxamide.

In some implementations, the salt comprises at least one of L-malate, citrate, hydrochloride, phosphate or lactate salt of (Z)—N-[2-(diethylamino)ethyl]-2-methyl-7-(1,2-dihydro-5-fluoro-2-oxo-3H-indol-3-ylidene)-4,5,6,7-tetrahydro-1H-indol-3-carboxamide.

In some implementations, the salt comprises at least one of L-tartrate, fumarate, sulfate, hydrobromate, succinate, acetate, p-toluenesulfonate, or maleate salt of (Z)—N-[2-(diethylamino)ethyl]-2-methyl-7-(1,2-dihydro-5-fluoro-2-oxo-3H-indol-3-ylidene)-4,5,6,7-tetrahydro-1H-indol-3-carboxamide.

In some implementations, the salt comprises at least one of L-tartrate, benzenesulfonate, L-mandelate, succinate, acetate or methanesulfonate salt of (Z)—N-[2-(diethylamino)ethyl]-2-methyl-7-(1,2-dihydro-5-fluoro-2-oxo-3H-indol-3-ylidene)-4,5,6,7-tetrahydro-1H-indol-3-carboxamide.

In some implementations, the salt comprises at least one of L-tartrate, succinate or acetate salt of (Z)—N-[2-(diethylamino)ethyl]-2-methyl-7-(1,2-dihydro-5-fluoro-2-oxo-3H-indol-3-ylidene)-4,5,6,7-tetrahydro-1H-indol-3-carboxamide.

In some implementations, the salt comprises L-malate salt of (Z)—N-[2-(diethylamino)ethyl]-2-methyl-7-(1,2-dihydro-5-fluoro-2-oxo-3H-indol-3-ylidene)-4,5,6,7-tetrahydro-1H-indol-3-carb oxamide.

In some implementations, the salt comprises citrate salt of (Z)—N-[2-(diethylamino)ethyl]-2-methyl-7-(1,2-dihydro-5-fluoro-2-oxo-3H-indol-3-ylidene)-4,5,6,7-tetrahydro-1H-indol-3-carboxamide.

In some implementations, the salt comprises hydrochloride salt of (Z)—N-[2-(diethylamino)ethyl]-2-methyl-7-(1,2-dihydro-5-fluoro-2-oxo-3H-indol-3-ylidene)-4,5,6,7-tetrahydro-1H-indol-3-carboxamide.

In some implementations, the salt comprises phosphate salt of (Z)—N-[2-(diethylamino)ethyl]-2-methyl-7-(1,2-dihydro-5-fluoro-2-oxo-3H-indol-3-ylidene)-4,5,6,7-tetrahydro-1H-indol-3-carboxamide.

In some implementations, the salt comprises lactate salt of (Z)—N-[2-(diethylamino)ethyl]-2-methyl-7-(1,2-dihydro-5-fluoro-2-oxo-3H-indol-3-ylidene)-4,5,6,7-tetrahydro-1H-indol-3-carboxamide.

In another aspect, a pharmaceutical composition is provided, comprising the salt of claim 1 and a pharmaceutically acceptable carrier or excipient.

In some implementations, the salt comprises at least one of L-malate, hydrochloride, phosphate, L-tartrate, benzenesulfonate, sulfate, methanesulfonate, succinate, citrate, fumarate, p-toluenesulfonate, hydrobromate, L-mandelate, lactate, acetate or maleate salt of (Z)—N-[2-(diethylamino)ethyl]-2-methyl-7-(1,2-dihydro-5-fluoro-2-oxo-3H-indol-3-ylidene)-4,5,6,7-tetrahydro-1H-indol-3-carboxamide.

In some implementations, the salt comprises at least one of L-malate, citrate, hydrochloride, phosphate or lactate salt of (Z)—N-[2-(diethylamino)ethyl]-2-methyl-7-(1,2-dihydro-5-fluoro-2-oxo-3H-indol-3-ylidene)-4,5,6,7-tetrahydro-1H-indol-3-carboxamide.

In some implementations, the salt is the L-malate salt of (Z)—N-[2-(diethylamino)ethyl]-2-methyl-7-(1,2-dihydro-5-fluoro-2-oxo-3H-indol-3-ylidene)-4,5,6,7-tetrahydro-1H-indol-3-carboxamide.

In another aspect, a method of treating proliferative diseases or malignant tumors is provided, the method comprising: administering a therapeutically effective amount of an acid addition salt of (Z)—N-[2-(diethylamino)ethyl]-2-methyl-7-(1,2-dihydro-5-fluoro-2-oxo-3H-indol-3-ylidene)-4,5,6,7-tetrahydro-1H-indol-3-carboxamide to a subject in need thereof.

In some implementations, the salt comprises at least one of L-malate, hydrochloride, phosphate, L-tartrate, benzenesulfonate, sulfate, methanesulfonate, succinate, citrate, fumarate, p-toluenesulfonate, hydrobromate, L-mandelate, lactate, acetate or maleate salt of (Z)—N-[2-(diethylamino)ethyl]-2-methyl-7-(1,2-dihydro-5-fluoro-2-oxo-3H-indol-3-ylidene)-4,5,6,7-tetrahydro-1H-indol-3-carboxamide.

In some implementations, the salt comprises at least one of L-malate, citrate, hydrochloride, phosphate or lactate salt of (Z)—N-[2-(diethylamino)ethyl]-2-methyl-7-(1,2-dihydro-5-fluoro-2-oxo-3H-indol-3-ylidene)-4,5,6,7-tetrahydro-1H-indol-3-carboxamide.

In some implementations, the salt comprises L-malate salt of (Z)—N-[2-(diethylamino)ethyl]-2-methyl-7-(1,2-dihydro-5-fluoro-2-oxo-3H-indol-3-ylidene)-4,5,6,7-tetrahydro-1H-indol-3-carboxamide.

In another aspect, a composition is provided, comprising at least two of L-malate, hydrochloride, phosphate, L-tartrate, benzenesulfonate, sulfate, methanesulfonate, succinate, citrate, fumarate, p-toluenesulfonate, hydrobromate, L-mandelate, lactate, acetate and maleate salts of (Z)—N-[2-(diethylamino)ethyl]-2-methyl-7-(1,2-dihydro-5-fluoro-2-oxo-3H-indol-3-ylidene)-4,5,6,7-tetrahydro-1H-indol-3-carboxamide.

DETAILED DESCRIPTION

The present invention relates to a pharmaceutically active compound (Z)—N-[2-(diethylamino)ethyl]-2-methyl-7-(1,2-dihydro-5-fluoro-2-oxo-3H-indol-3-ylidene)-4,5,6,7-tetrahydro-1H-indol-3-carboxamide in the form of acid addition salts.

The present invention is further described below through embodiments, but the present invention is not limited thereto.

By forming salts from the medicament in the presence of a molecule or ion carrying charge opposite to the medicament, some undesirable physicochemical or biopharmaceutical properties can be improved. For example, the solubility or dissolution of the medicament is changed, the hygroscopicity is reduced, the stability is improved, the melting point is changed, the grinding performance is improved, the preparation and purification become more convenient, the permeability is increased, slow and controlled release or targeted drug delivery is achieved, and the taste and compatibility are improved. Each of the salt forms of the medicament has unique natures, and the finally determined salt form is a balance between the physicochemical properties and biopharmaceutical properties. For physicochemical properties, the selected salt form of medicament needs to first meet the following requirements: high crystallinity, low hygroscopicity, stability of an aqueous solution at different pH values (determined by the use of the medicament), excellent chemical and solid-state stability in accelerated test (that is, minimal chemical degradation and solid-state variation at 40° C. and 75% relative humidity). Although it is known that preparations in the salt form can improve the physical or pharmaceutical properties of pharmaceutically active basic compounds, it is impossible to predict which salt form may be advantageous for particular purpose before actual preparation and characterization of the salt forms. Therefore, selection of the salt form of medicament is critical for successful development of drugs, which requires a well-designed screening strategy for finding the salt form having the target performance.

The present invention relates to the preparation of various salt compounds of pharmaceutically active compound (Z)—N-[2-(diethylamino)ethyl]-2-methyl-7-(1,2-dihydro-5-fluoro-2-oxo-3H-indol-3-ylidene)-4,5,6,7-tetrahydro-1H-indol-3-carboxamide, and the measurement of physicochemical and biological properties of the salt compounds, in which the physicochemical and biological properties include solubility, hygroscopicity, plasma exposure of the pharmaceutically active compound in animal body and anti-tumor effects in animal body.

As used herein, the term "pharmaceutical composition" refers to a mixture of the salt compound of (Z)—N-[2-(diethylamino)ethyl]-2-methyl-7-(1,2-dihydro-5-fluoro-2-oxo-3H-indol-3-ylidene)-4,5,6,7-tetrahydro-1H-indol-3-carboxamide with other chemical components such as a pharmaceutically acceptable carrier and excipient. The pharmaceutical composition is aimed at promoting administration of the compound to an organism.

The "pharmaceutically acceptable carrier" refers to a carrier or diluent having no significant stimulation to the organism and having no interference to the biological activities and properties of the administered compound.

The "excipient" refers to an inactive substance added into the pharmaceutical composition for the purpose of further facilitating administration of the compound. Examples of the excipient include, but are not limited to, calcium carbonate, calcium phosphate, a variety of saccharides and a variety of types of starch, cellulose derivatives, gelatin, vegetable oils and polyethylene glycol.

The "hygroscopicity" herein refers to a property indicating the moist absorption capability of the compound at a certain temperature and humidity.

The present invention relates to the acid addition salts of (Z)—N-[2-(diethylamino)ethyl]-2-methyl-7-(1,2-dihydro-5-fluoro-2-oxo-3H-indol-3-ylidene)-4,5,6,7-tetrahydro-1H-indol-3-carboxamide, selected from L-malate, hydrochloride, phosphate, L-tartrate, benzenesulfonate, sulfate, methanesulfonate, succinate, citrate, fumarate, p-toluenesulfonate, hydrobromate, L-mandelate, lactate, acetate and maleate salts, having a structure represented by Formula II below.

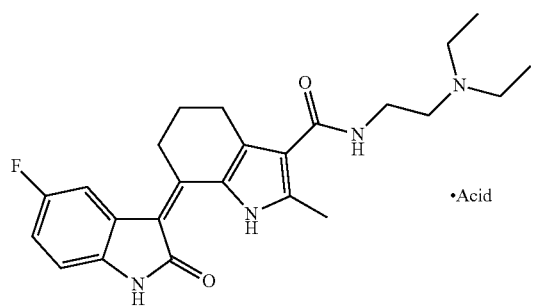

Formula II

Disclosed is a method for preparation of salt compounds of (Z)—N-[2-(diethylamino)ethyl]-2-methyl-7-(1,2-dihydro-5-fluoro-2-oxo-3H-indol-3-ylidene)-4,5,6,7-tetrahydro-1H-indol-3-carboxamide, including dissolving (Z)—N-[2-(diethylamino)ethyl]-2-methyl-7-(1,2-dihydro-5-fluoro-2-oxo-3H-indol-3-ylidene)-4,5,6,7-tetrahydro-1H-indol-3-carboxamide in a mixed solvent of acetonitrile and dichloromethane, adding a certain amount of an acid, heating the reaction at reflux, filtering the solution, concentrating the filtrate to dryness, and washing the resulting product with anhydrous ethanol to give the salt compound.

Further, solubility and hygroscopicity of the different salt compounds are measured, and the acid addition salt of (Z)—N-[2-(diethylamino)ethyl]-2-methyl-7-(1,2-dihydro-5-fluoro-2-oxo-3H-indol-3-ylidene)-4,5,6,7-tetrahydro-1H-indol-3-carboxamide is preferably selected from L-malate, benzenesulfonate, L-mandelate, succinate, L-malate, citrate, hydrochloride, phosphate and lactate, and more preferably selected from L-malate, citrate, hydrochloride, phosphate and lactate.

The method for measuring the hygroscopicity may include: placing a certain amount of a sample to be tested into a precisely weighed glass weighing bottle ($m_1$) with a plug and precisely weighing ($m_2$); placing the opened weighing bottle into a thermostatic dryer (with saturated ammonium sulfate solution placed at the bottom, with a relative humidity of 80±2%) at 25±1° C. for 24 hours; covering the weighing bottle with the plug and precisely weighing ($m_3$), and calculating the percent of weight gain of the sample to be tested according to the following equation:

$$\text{the percent of weight gain} = \frac{m_3 - m_2}{m_2 - m_1} \times 100\%.$$

The method for measuring the solubility may include: precisely weighing about 100 mg sample to be tested into a 100 ml graduated flask at 25° C.; adding an appropriate amount of a solvent [acetonitrile-water (80:20)] to dissolve the sample under ultrasonic sound and diluting the solvent to a given scale; shaking up; precisely measuring 10 μl solution and loading into a liquid chromatograph, recording chromatogram and measuring a peak area $S_{control}$; weighing 10 ml purified water and placing into a 25 ml Kjeldahl flask; gradually adding the sample to be tested at 25° C. until an insoluble solid appears in the solution; treating under ultrasonic sound for 30 min; filtering off the insoluble solid; precisely measuring 10 μl filtrate and loading into the liquid chromatograph, recording chromatogram, measuring the peak area $S_{test}$, and calculating the solubility of the sample according to the following equation:

$$\text{the solubility of the sample} = \frac{S_{test}}{S_{control}} \times 1 \text{ mg/ml}.$$

Further, according to comparison of plasma exposures of the pharmaceutically active compound in rats after oral administration of the different salt compounds at the same dose, L-malate of (Z)—N-[2-(diethylamino)ethyl]-2-methyl-7-(1,2-dihydro-5-fluoro-2-oxo-3H-indol-3-ylidene)-4,5,6,7-tetrahydro-1H-indol-3-carboxamide is preferred.

The present invention also relates to a use of the salts of (Z)—N-[2-(diethylamino)ethyl]-2-methyl-7-(1,2-dihydro-5-fluoro-2-oxo-3H-indol-3-ylidene)-4,5,6,7-tetrahydro-1H-indol-3-carboxamide in the preparation of medicaments for the treatment of proliferative diseases or malignant tumors, as well as a pharmaceutical composition, including the salt compounds of (Z)—N-[2-(diethylamino)ethyl]-2-methyl-7-(1,2-dihydro-5-fluoro-2-oxo-3H-indol-3-ylidene)-4,5,6,7-tetrahydro-1H-indol-3-carboxamide and a pharmaceutically acceptable carrier or excipient.

Source and Specification of Starting Materials:

(Z)—N-[2-(diethylamino)ethyl]-2-methyl-7-(1,2-dihydro-5-fluoro-2-oxo-3H-indol-3-ylidene)-4,5,6,7-tetrahydro-1H-indol-3-carboxamide is synthesized according to the processes in the document, see Tang Feng et al., WO2008/067756 (2008). The other reagents and solvents are commercially available, which are chemical grade or analytical grade, and the reagents used for HPLC measurement are chromatographic grade.

EXAMPLE 1

(Z)—N-[2-(diethylamino)ethyl]-2-methyl-7-(1,2-dihydro-5-fluoro-2-oxo-3H-indol-3-ylidene)-4,5,6,7-tetrahydro-1H-indol-3-carboxamide L-malate 8.49 g (20 mmol) (Z)—N-[2-(diethylamino)ethyl]-2-methyl-7-(1,2-dihydro-5-fluoro-2-oxo-3H-indol-3-ylidene)-4,5,6,7-tetrahydro-1H-indol-3-carboxamide was added to a mixture of 500 ml acetonitrile and 90 ml dichloromethane. The mixture was treated under ultrasonic sound to uniform dispersion. 3.22 g (24 mmol) L-malic acid was added and the solution was heated to reflux with stirring under nitrogen atmosphere. After reaction for 1 h, the resulting solution was filtered while being hot, and the filtrate was concentrated at reduced pressure to dryness, and the resulting product was added to 60 ml anhydrous ethanol and treated under ultrasonic sound to uniform dispersion. Then the solution was filtered, and the filter cake was dried at 40° C. under vacuum, to give the title compound as yellow solid (10.39 g, 18.6 mmol, yield 93%).

$^1$H NMR (DMSO-$d_6$) δ ppm: 1.15(6H,t, J=7.2 Hz), 1.93 (2H, m), 2.36(1H, dd, J=15.5, 5.7 Hz), 2.47(3H, s), 2.57(1H, dd, J=15.5, 7.7 Hz), 2.83(2H, t, J=5.8 Hz), 2.99(4H, q, J=7.2 Hz), 3.02(2H, m), 3.03(2H, m), 3.50(2H, q, J=6.1 Hz), 4.03 (1H, dd J=7.7, 5.7 Hz), 6.84(1H, dd, J=8.5, 5.1 Hz), 6.91 (1H, td, J=8.6, 2.2 Hz), 7.37(1H, dd, J=8.9, 2.0 Hz), 7.55(1 H, t, J=5.5 Hz), 10.01(3H, brs), 10.89(1H, s), 14.58(1H, s).

EXAMPLE 2

(Z)—N-[2-(diethylamino)ethyl]-2-methyl-7-(1,2-dihydro-5-fluoro-2-oxo-3H-indol-3-ylidene)-4,5,6,7-tetrahydro-1H-indol-3-carboxamide hydrochloride 4.25 g (10 mmol) (Z)—N-[2-(diethylamino)ethyl]-2-methyl-7-(1,2-dihydro-5-fluoro-2-oxo-3H-indol-3-ylidene)-4,5,6,7-tetrahydro-1H-indol-3-carboxamide was added to a mixture of 250 ml acetonitrile and 50 ml dichloromethane. The mixture was treated under ultrasonic sound to uniform dispersion. 8 ml (1.50 mol/L) HCl in acetonitrile was added and the solution was heated to reflux with stirring under nitrogen atmosphere. After reaction for 1 h, the resulting solution was filtered while being hot, and the filtrate was concentrated at reduced pressure to dryness, added to 30 ml anhydrous ethanol and treated under ultrasonic sound to uniform dispersion. Then the solution was filtered, and the filter cake was dried at 40° C. under vacuum, to give the title compound as yellow solid (4.16 g, 9 mmol, yield 90%).

$^1$H NMR (DMSO-$d_6$) δ ppm: 1.25(6H, t, J=7.1 Hz), 1.94 (2H, m), 2.50(3H, s), 2.88(2H, t, J=5.7 Hz), 3.07(2H, t, J=5.9

Hz), 3.60(2H, q, J=6.1 Hz), 6.88(1H, dd, J=8.6, 5.1 Hz), 6.95(1H, td, J=8.6, 2.3 Hz), 7.43(1H, dd, J=10.8, 2.2 Hz), 7.85(1H, t, J=5.7 Hz), 10.48(1H, brs), 10.96(1H, s), 14.61 (1H, s).

EXAMPLE 3

(Z)—N-[2-(diethylamino)ethyl]-2-methyl-7-(1,2-dihydro-5-fluoro-2-oxo-3H-indol-3-ylidene)-4,5,6,7-tetrahydro-1H-indol-3-carboxamide phosphate 4.25 g (10 mmol) (Z)—N-[2-(diethylamino)ethyl]-2-methyl-7-(1,2-dihydro-5-fluoro-2-oxo-3H-indol-3-ylidene)-4,5,6,7-tetrahydro-1H-indol-3-carboxamide was added to a mixture of 250 ml acetonitrile and 50 ml dichloromethane. The mixture was treated under ultrasonic sound to uniform dispersion. 1.18 g (12 mmol) phosphoric acid was added and the solution was heated to reflux with stirring under nitrogen atmosphere. After reaction for 1 h, the resulting solution was filtered while being hot, and the filtrate was concentrated at reduced pressure to dryness, added to 30 ml anhydrous ethanol and treated under ultrasonic sound to uniform dispersion. Then the solution was filtered, and the filter cake was dried at 40° C. under vacuum, to give the title compound as yellow solid (4.65 g, 8.9 mmol, yield 89%).
$^1$H NMR (DMSO-$d_6$) δ ppm: 1.12(6H, t, J=6.5 Hz), 1.93 (2H, m), 2.47(3H, s), 2.85(8H, m), 3.05(2H, m), 3.46(2H, m), 6.86(1H, dd, J=8.4, 5.1 Hz), 6.93(1H, m), 7.14(3H, brs), 7.41(1H, m), 7.61(1H, m), 10.95(1H, s), 14.57(1H, s).

EXAMPLE 4

(Z)—N-[2-(diethylamino)ethyl]-2-methyl-7-(1,2-dihydro-5-fluoro-2-oxo-3H-indol-3-ylidene)-4,5,6,7-tetrahydro-1H-indol-3-carboxamide L-tartrate 4.25 g (10 mmol) (Z)—N-[2-(diethylamino)ethyl]-2-methyl-7-(1,2-dihydro-5-fluoro-2-oxo-3H-indol-3-ylidene)-4,5,6,7-tetrahydro-1H-indol-3-carboxamide was added to a mixture of 250 ml acetonitrile and 50 ml dichloromethane. The mixture was treated under ultrasonic sound to uniform dispersion. 1.76 g (12 mmol) L-tartaric acid was added and the solution was heated to reflux with stirring under nitrogen atmosphere. After reaction for 1 h, the resulting solution was filtered while being hot, and the filtrate was concentrated at reduced pressure to dryness, added to 30 ml anhydrous ethanol and treated under ultrasonic sound to uniform dispersion. Then the solution was filtered, and the filter cake was dried at 40 C under vacuum, to give the title compound as yellow solid (5.20 g, 9.1 mmol, yield 91%).
$^1$H NMR (DMSO-$d_6$) δ ppm: 1.10(6H, t, J=6.9 Hz), 1.94 (2H, m), 2.47(3H, s), 2.86(8H, m), 3.07(2H, m), 3.43(2H, m), 4.02(2H, s), 6.87(1H, dd, J=8.5, 5.3 Hz), 6.95(1H, td, J=8.9, 1.8 Hz), 7.42(1H, m), 7.50(1H, m), 10.92(1H, s), 14.58(1H, s).

EXAMPLE 5

(Z)—N-[2-(diethylamino)ethyl]-2-methyl-7-(1,2-dihydro-5-fluoro-2-oxo-3H-indol-3-ylidene)-4,5,6,7-tetrahydro-1H-indol-3-carboxamide benzenesulfonate 4.25 g (10 mmol) (Z)—N-[2-(diethylamino)ethyl]-2-methyl-7-(1,2-dihydro-5-fluoro-2-oxo-3H-indol-3-ylidene)-4,5,6,7-tetrahydro-1H-indol-3-carboxamide was added to a mixture of 250 ml acetonitrile and 50 ml dichloromethane. The mixture was treated under ultrasonic sound to uniform dispersion. 1.90 g (12 mmol) benzenesulfonic acid was added and the solution was heated to reflux with stirring under nitrogen atmosphere. After reaction for 1 h, the resulting solution was filtered while being hot, and the filtrate was concentrated at reduced pressure to dryness, added to 30 ml anhydrous ethanol and treated under ultrasonic sound to uniform dispersion. Then the solution was filtered, and the filter cake was dried at 40° C. under vacuum, to give the title compound as yellow solid (4.96 g, 8.5 mmol, yield 85%).
$^1$H NMR (DMSO-$d_6$) δ ppm: 1.23(6H, t, J=7.2 Hz), 1.94 (2H, m), 2.49(3H, s), 2.86(2H, t, J=5.9 Hz), 3.08(2H, t, J=5.7 Hz), 3.19(6H, m), 3.58(2H, q, J=6.4 Hz), 6.88(1H, dd, J=8.5, 5.1 Hz), 6.96(1H, td, J=8.8, 2.3 Hz), 7.30(3H, m), 7.43(2H, m), 7.71(1H, t, J=5.5 Hz), 10.94(1H, s), 14.62(1H, s).

EXAMPLE 6

(Z)—N-[2-(diethylamino)ethyl]-2-methyl-7-(1,2-dihydro-5-fluoro-2-oxo-3H-indol-3-ylidene)-4,5,6,7-tetrahydro-1H-indol-3-carboxamide sulfate 4.25 g (10 mmol) (Z)—N-[2-(diethylamino)ethyl]-2-methyl-7-(1,2-dihydro-5-fluoro-2-oxo-3H-indol-3-ylidene)-4,5,6,7-tetrahydro-1H-indol-3-carboxamide was added to a mixture of 250 ml acetonitrile and 50 ml dichloromethane. The mixture was treated under ultrasonic sound to uniform dispersion. 1.19 g (12 mmol) concentrated sulfuric acid was added and the solution was heated to reflux with stirring under nitrogen atmosphere. After reaction for 1 h, the resulting solution was filtered while being hot, and the filtrate was concentrated at reduced pressure to dryness, added to 30 ml anhydrous ethanol and treated under ultrasonic sound to uniform dispersion. Then the solution was filtered, and the filter cake was dried at 40° C. under vacuum, to give the title compound as yellow solid (4.60 g, 8.8 mmol, yield 88%).
$^1$H NMR (DMSO-$d_6$) δ ppm: 1.24(6H, t, J=7.1 Hz), 1.95 (2H, m), 2.50(3H, s), 2.86(2H, t, J=5.8 Hz), 3.07(2H, t, J=5.9 Hz), 3.22(6H, m), 3.57(2H, m), 6.84(1H, dd, J=8.5, 5.2 Hz), 6.96(1H, td, J=9.2, 2.1 Hz), 7.43(1H, m), 7.62(1H, t, J=5.6 Hz), 9.12(2H, brs), 10.93(1H, s), 14.63(1H, s).

EXAMPLE 7

(Z)—N-[2-(diethylamino)ethyl]-2-methyl-7-(1,2-dihydro-5-fluoro-2-oxo-3H-indol-3-ylidene)-4,5,6,7-tetrahydro-1H-indol-3-carboxamide methanesulfonate 4.25 g (10 mmol) (Z)—N-[2-(diethylamino)ethyl]-2-methyl-7-(1,2-dihydro-5-fluoro-2-oxo-3H-indol-3-ylidene)-4,5,6,7-tetrahydro-1H-indol-3-carboxamide was added to a mixture of 250 ml acetonitrile and 50 ml dichloromethane. The mixture was treated under ultrasonic sound to uniform dispersion. 1.11 g (11.5 mmol) methanesulfonic acid was added and the solution was heated to reflux with stirring under nitrogen atmosphere. After reaction for 1 h, the resulting solution was filtered while being hot, and the filtrate was concentrated at reduced pressure to dryness, added to 30 ml anhydrous ethanol and treated under ultrasonic sound to uniform dispersion. Then the solution was filtered, and the filter cake was dried at 40° C. under vacuum, to give the title compound as orange solid (4.33 g, 8.3 mmol, yield 83%).
$^1$H NMR (DMSO-$d_6$) δ ppm: 1.24(6H, t, J=7.2 Hz), 1.95 (2H, m), 2.35(3H, s), 2.49(3H, s), 2.86(2H, m), 3.08(2H, m), 3.23(6H, m), 3.03(2H, m), 3.57(2H, m), 6.92(2H, m), 7.43 (1H, m), 7.64(1H, m), 9.93(1H, m), 10.94(1H, s), 14.6(1H, s).

EXAMPLE 8

(Z)—N-[2-(diethylamino)ethyl]-2-methyl-7-(1,2-dihydro-5-fluoro-2-oxo-3H-indol-3-ylidene)-4,5,6,7-tetrahydro-1H-indol-3-carboxamide succinate 4.25 g (10 mmol) (Z)—N-[2-(diethylamino)ethyl]-2-methyl-7-(1,2-dihydro-5-fluoro-2-oxo-3H-indol-3-ylidene)-4,5,6,7-tetrahydro-1H-indol-3-carboxamide was added to a mixture of 250 ml acetonitrile and 50 ml dichloromethane. The mixture was treated under ultrasonic sound to uniform dispersion. 1.36 g (11.5 mmol) succinic acid was added and the solution was heated to reflux with stirring under nitrogen atmosphere. After reaction for 1 h, the resulting solution was filtered while being hot, and the filtrate was concentrated at reduced pressure to dryness, added to 30 ml anhydrous ethanol and treated under ultrasonic sound to uniform dispersion. Then the solution was filtered, and the filter cake was dried at 40° C. under vacuum, to give the title compound as yellow solid (4.73 g, 8.7 mmol, yield 87%).

$^1$H NMR (DMSO-$d_6$) δ ppm: 1.03(6H, t, J=7.1 Hz), 1.94 (2H, m), 2.38(4H, s), 2.47(3H, s), 2.65(6H, m), 2.84(2H, t, J=5.8 Hz), 3.07(2H, t, J=5.9 Hz), 3.34(2H, q, J=6.3 Hz), 6.86(1H, dd, J=8.5, 5.2 Hz), 6.95(1H, td, J=8.9, 2.3 Hz), 7.32(1H, m), 7.44(1H, dd, J=2.3, 8.7 Hz), 10.91(1H, s), 14.57 (1H, s).

EXAMPLE 9

(Z)—N-[2-(diethylamino)ethyl]-2-methyl-7-(1,2-dihydro-5-fluoro-2-oxo-3H-indol-3-ylidene)-4,5,6,7-tetrahydro-1H-indol-3-carboxamide citrate 4.25 g (10 mmol) (Z)—N-[2-(diethylamino)ethyl]-2-methyl-7-(1,2-dihydro-5-fluoro-2-oxo-3H-indol-3-ylidene)-4,5,6,7-tetrahydro-1H-indol-3-carboxamide was added to a mixture of 250 ml acetonitrile and 50 ml dichloromethane. The mixture was treated under ultrasonic sound to uniform dispersion. 2.31 g (12 mmol) citric acid was added and the solution was heated to reflux with stirring under nitrogen atmosphere. After reaction for 1 h, the resulting solution was filtered while hot, and the filtrate was concentrated at reduced pressure to dryness, added to 30 ml anhydrous ethanol and treated under ultrasonic sound to uniform dispersion. Then the solution was filtered, and the filter cake was dried at 40° C. under vacuum, to give the title compound as yellow solid (5.68 g, 9.2 mmol, yield 92%).

$^1$H NMR (DMSO-$d_6$) δ ppm: 1.17(6H, t, J=7.2 Hz), 1.95 (2H, m), 2.49(3H, s), 2.52(2H, d, J=15.2 Hz), 2.60(2H, d, J=15.2 Hz), 2.85(2H, t, J=5.9 Hz), 3.07(8H, m), 3.51(2H, m), 6.88(1H, dd, J=8.4, 5.0 Hz), 6.96(1H, td, J=8.7, 2.4 Hz), 7.43(1H, dd, J=10.8, 2.2 Hz), 7.53(1H, m), 10.92(4H, brs), 14.61(1H, s).

EXAMPLE 10

(Z)—N-[2-(diethylamino)ethyl]-2-methyl-7-(1,2-dihydro-5-fluoro-2-oxo-3H-indol-3-ylidene)-4,5,6,7-tetrahydro-1H-indol-3-carboxamide fumarate 4.25 g (10 mmol) (Z)—N-[2-(diethylamino)ethyl]-2-methyl-7-(1,2-dihydro-5-fluoro-2-oxo-3H-indol-3-ylidene)-4,5,6,7-tetrahydro-1H-indol-3-carboxamide was added to a mixture of 250 ml acetonitrile and 50 ml dichloromethane. The mixture was treated under ultrasonic sound to uniform dispersion. 1.36 g (11.7 mmol) fumaric acid was added and the solution was heated to reflux with stirring under nitrogen atmosphere. After reaction for 1 h, the resulting solution was filtered while being hot, and the filtrate was concentrated at reduced pressure to dryness, added to 30 ml anhydrous ethanol and treated under ultrasonic sound to uniform dispersion. Then the solution filtered, and the filter cake was dried at 40° C. under vacuum, to give the title compound as yellow solid (5.14 g, 9.5 mmol, yield 95%).

$^1$H NMR (DMSO-$d_6$) δ ppm: 1.45(6H, t, J=7.0 Hz), 1.94 (2H, m), 2.47(3H, s), 2.71(6H, m), 2.84(2H, t, J=5.7 Hz), 3.07(2H, t, J=5.9 Hz), 3.36(2H, q, J=6.2 Hz), 6.50(2H, s), 6.87(1H, dd, J=8.5, 5.2 Hz), 6.95(1H, td, J=8.8, 2.1 Hz), 7.42(2H, m), 10.92(1H, s), 14.57(1H, s).

EXAMPLE 11

(Z)—N-[2-(diethylamino)ethyl]-2-methyl-7-(1,2-dihydro-5-fluoro-2-oxo-3H-indol-3-ylidene)-4,5,6,7-tetrahydro-1H-indol-3-carboxamide p-toluenesulfonate 4.25 g (10 mmol) (Z)—N-[2-(diethylamino)ethyl]-2-methyl-7-(1,2-dihydro-5-fluoro-2-oxo-3H-indol-3-ylidene)-4,5,6,7-tetrahydro-1H-indol-3-carboxamide was added to a mixture of 250 ml acetonitrile and 50 ml dichloromethane. The mixture was treated under ultrasonic sound to uniform dispersion. 2.21 g (13 mmol) p-toluenesulfonic acid was added and the solution was heated to reflux with stirring under nitrogen atmosphere. After reaction for 1 h, the resulting mixture was filtered while being hot, and the filtrate was concentrated at reduced pressure to dryness, added to 30 ml anhydrous ethanol and treated under ultrasonic sound to uniform dispersion. Then the solution was filtered, and the filter cake was dried at 40° C. under vacuum, to give the title compound as yellow solid (5.43 g, 9.1 mmol, yield 91%).

$^1$H NMR (DMSO-$d_6$) δ ppm: 1.23(6H, t, J=7.3 Hz), 1.94 (2H, m), 2.27(3H, s), 2.49(3H, s), 2.85(2H, t, J=5.7 Hz), 3.08(2H, t, J=5.6 Hz), 3.22(6H, m), 3.56(2H, q, J=5.8 Hz), 6.88(1H, dd, J=8.4, 5.0 Hz), 6.96(1H, td, J=8.9, 2.3 Hz), 7.10(2H, m), 7.46(3H, m), 7.46(1H, t, J=5.3 Hz), 9.94(1H, brs), 10.94(1H, s), 14.63(1H, s).

EXAMPLE 12

(Z)—N-[2-(diethylamino)ethyl]-2-methyl-7-(1,2-dihydro-5-fluoro-2-oxo-3H-indol-3-ylidene)-4,5,6,7-tetrahydro-1H-indol-3-carboxamide hydrobromate 4.25 g (10 mmol) (Z)—N-[2-(diethylamino)ethyl]-2-methyl-7-(1,2-dihydro-5-fluoro-2-oxo-3H-indol-3-ylidene)-4,5,6,7-tetrahydro-1H-indol-3-carboxamide was added to a mixture of 250 ml acetonitrile and 50 ml dichloromethane. The mixture was treated under ultrasonic sound to uniform dispersion. 2.39 g 40% (12 mmol) hydrobromic acid in water was added and the solution was heated to reflux with stirring under nitrogen atmosphere. After reaction for 1 h, the resulting mixture was filtered while being hot, and the filtrate was concentrated at reduced pressure to dryness, added to 30 ml anhydrous ethanol and treated under ultrasonic sound to uniform dispersion. Then the solution was filtered, and the filter cake was dried at 40° C. under vacuum, to give the title compound as yellow solid (4.20 g, 8.3 mmol, yield 83%).

$^1$H NMR (DMSO-$d_6$) δ ppm: 1.25(6H, t, J=1.2 Hz), 1.94 (2H, m), 2.50(3H, s), 2.88(2H, t, J=5.6 Hz), 3.06(2H, t, J=5.8 Hz), 3.22(6H, m), 3.59(2H, q, J=5.9 Hz), 6.87(1H, dd, J=8.4, 5.2 Hz), 6.96(1H, td, J=9.0, 2.3 Hz), 7.43(1H, m), 7.69(1H, t, J=5.6 Hz), 9.40(1H, brs), 10.93(1H, s), 14.62(1H, s).

EXAMPLE 13

(Z)—N-[2-(diethylamino)ethyl]-2-methyl-7-(1,2-dihydro-5-fluoro-2-oxo-3H-indol-3-ylidene)-4,5,6,7-tetrahydro-1H-indol-3-carboxamide L-mandelate 4.25 g (10 mmol) (Z)—N-[2-(diethylamino)ethyl]-2-methyl-7-(1,2-dihydro-5-fluoro-2-oxo-3H-indol-3-ylidene)-4,5,6,7-tetrahydro-1H-indol-3-carboxamide was added to a mixture of 250 ml acetonitrile and 50 ml dichloromethane. The mixture was treated under ultrasonic sound to uniform dispersion. 1.81 g (12 mmol) L-mandelic acid was added and the solution was heated to reflux with stirring under nitrogen atmosphere. After reaction for 1 h, the resulting mixture was filtered while hot, and the filtrate was concentrated at reduced pressure to dryness, added to 30 ml anhydrous ethanol and treated under ultrasonic sound to uniform dispersion, then solution was filtered, and the filter cake was dried at 40° C. under vacuum, to give the title compound as orange solid (5.02 g, 8.7 mmol, yield 87%).
$^1$H NMR (DMSO-$d_6$) δ ppm: 1.06(6H, t, J=7.0 Hz), 1.94 (2H, m), 2.46(3H, s), 2.79(8H, m), 3.07(2H, m), 3.39(2H, m), 6.91(2H, m), 7.27(3H, m), 7.38(2H, m), 7.46(2H, m), 10.94 (1H, s), 14.58(1H, s).

EXAMPLE 14

(Z)—N-[2-(diethylamino)ethyl]-2-methyl-7-(1,2-dihydro-5-fluoro-2-oxo-3H-indol-3-ylidene)-4,5,6,7-tetrahydro-1H-indol-3-carboxamide lactate 4.25 g (10 mmol) (Z)—N-[2-(diethylamino)ethyl]-2-methyl-7-(1,2-dihydro-5-fluoro-2-oxo-3H-indol-3-ylidene)-4,5,6,7-tetrahydro-1H-indol-3-carboxamide was added to a mixture of 250 ml acetonitrile and 50 ml dichloromethane. The mixture was treated under ultrasonic sound to uniform dispersion. 1.08 g (12 mmol) lactic acid was added and the solution was heated to reflux with stirring under nitrogen atmosphere. After reaction for 1 h, the resulting mixture was filtered while being hot, and the filtrate was concentrated at reduced pressure to dryness, added to 30 ml anhydrous ethanol and treated under ultrasonic sound to uniform dispersion. Then the solution was filtered, and the filter cake was dried at 40° C. under vacuum, to give the title compound as orange solid (4.12 g, 8 mmol, yield 80%).
$^1$H NMR (DMSO-$d_6$) δ ppm: 1.03(6H, t, J=7.2 Hz), 1.20 (3H, d, J=6.8 Hz), 1.94(2H, m), 2.47(3H, s), 2.64(6H, m), 2.84(2H, t, J=5.7 Hz), 3.07(2H, t, J=5.6 Hz), 3.34(2H, q, J=6.4 Hz), 3.96(1H, q, J=6.8 Hz), 6.88(2H, m), 7.39(2H, m), 10.91(1H, s), 14.57(1H, s).

EXAMPLE 15

(Z)—N-[2-(diethylamino)ethyl]-2-methyl-7-(1,2-dihydro-5-fluoro-2-oxo-3H-indol-3-ylidene)-4,5,6,7-tetrahydro-1H-indol-3-carboxamide acetate 4.25 g (10 mmol) (Z)—N-[2-(diethylamino)ethyl]-2-methyl-7-(1,2-dihydro-5-fluoro-2-oxo-3H-indol-3-ylidene)-4,5,6,7-tetrahydro-1H-indol-3-carboxamide was added to a mixture of 250 ml acetonitrile and 50 ml dichloromethane. The mixture was treated under ultrasonic sound to uniform dispersion. 0.72 g (12 mmol) acetic acid was added and the solution was heated to reflux with stirring under nitrogen atmosphere. After reaction for 1 h, the resulting mixture was filtered while being hot, and the filtrate was concentrated at reduced pressure to dryness, added to 30 ml anhydrous ethanol and treated under ultrasonic sound to uniform dispersion. Then the solution was filtered, and the filter cake was dried at 40° C. under vacuum, to give the title compound as yellow solid (3.64 g, 7.5 mmol, yield 75%).
$^1$H NMR (DMSO-$d_6$) δ ppm: 0.98(6H, t, J=7.3 Hz), 1.91 (3H, s), 1.94(2H, m), 2.47(3H, s), 2.55(6H, m), 2.83(2H, t, J=6.0 Hz), 3.07(2H, t, J=6.0 Hz), 3.29(2H, q, J=6.5 Hz), 6.87(1H, dd, J=8.6, 5.2 Hz), 6.94(1H, td, J=9.1, 2.3 Hz), 7.22(1H, t, J=5.2), 7.43(1H, dd, J=5.5, 2.1 Hz), 10.89(1H, s), 14.56(1H, s).

EXAMPLE 16

(Z)—N-[2-(diethylamino)ethyl]-2-methyl-7-(1,2-dihydro-5-fluoro-2-oxo-3H-indol-3-ylidene)-4,5,6,7-tetrahydro-1H-indol-3-carboxamide maleate 4.25 g (10 mmol) (Z)—N-[2-(diethylamino)ethyl]-2-methyl-7-(1,2-dihydro-5-fluoro-2-oxo-3H-indol-3-ylidene)-4,5,6,7-tetrahydro-1H-indol-3-carboxamide was added to a mixture of 250 ml acetonitrile and 50 ml dichloromethane. The mixture was treated under ultrasonic sound to uniform dispersion. 1.39 g (12 mmol) maleic acid was added and the solution was heated to reflux with stirring under nitrogen atmosphere. After reaction for 1 h, the resulting mixture was filtered while being hot, and the filtrate was concentrated at reduced pressure to dryness, added to 30 ml anhydrous ethanol and treated under ultrasonic sound to uniform dispersion. Then the solution was filtered, and the filter cake was dried at 40° C. under vacuum, to give the title compound as yellow solid (4.87 g, 9 mmol, yield 90%).
$^1$H NMR (DMSO-$d_6$) δ ppm: 1.23(6H, t, J=6.8 Hz), 1.96 (2H, m), 2.49(3H, s), 2.86(2H, t, J=6.0 Hz), 3.10(2H, t, J=5.6 Hz), 3.22(4H, m), 3.34(2H, m), 3.56(2H, q, J=6.0 Hz), 6.02 (2H, s), 6.88(1H, dd, J=8.4, 5.2 Hz), 6.97(1H, td, J=8.8, 2.4 Hz), 7.45(1H, dd, J=10.8, 2.0 Hz), 7.61(1H, t, J=5.2), 10.96 (1H, s), 14.64(1H, s).

EXAMPLE 17

(Z)—N-[2-(diethylamino)ethyl]-2-methyl-7-(1,2-dihydro-5-fluoro-2-oxo-3H-indol-3-ylidene)-4,5,6,7-tetrahydro-1H-indol-3-carboxamide (pharmaceutically active compound) and L-tartrate, L-malate, hydrochloride, phosphate, benzenesulfonate, maleate, fumarate, L-mandelate, sulfate, p-toluenesulfonate, lactate, citrate, hydrobromate, succinate, acetate and methanesulfonate salts thereof were measured for the hygroscopicity.

The measurement method includes: placing a certain amount of sample to be tested into a precisely weighed glass weighing bottle ($m_1$) with a plug and precisely weighing ($m_2$); placing the opened weighing bottle in a thermostated dryer (with saturated ammonium sulfate solution placed at the bottom, with a relative humidity of 80±2%) at 25±1° C. for 24 hours; covering the weighing bottle with the plug and precisely weighing ($m_3$).

$$\text{The percent of weight gain} = \frac{m_3 - m_2}{m_2 - m_1} \times 100\%.$$

Characterization of the hygroscopicity and definition of the hygroscopic weight gain:

Deliquescence: sufficient moisture was absorbed to form liquid;

Strong hygroscopicity: hygroscopic weight gain was not less than 15%;

Hygroscopicity: hygroscopic weight gain was less than 15% and not less than 2%;

Slight hygroscopicity: hygroscopic weight gain was less than 2% and not less than 0.2%:

No or almost no hygroscopicity: hygroscopic weight gain was less than 0.2%.

TABLE 1

Substance to Be Tested and Their Hygroscopicity

| No. | Substance to Be Tested | Hygroscopicity |
|---|---|---|
| 1 | Pharmaceutically active compound | Almost no hygroscopicity |
| 2 | Citrate | Slight hygroscopicity |
| 3 | Hydrochloride | Almost no hygroscopicity |
| 4 | Phosphate | Slight hygroscopicity |
| 5 | L-tartrate | Slight hygroscopicity |
| 6 | Lactate | Hygroscopicity |
| 7 | Benzenesulfonate | Hygroscopicity |
| 8 | Fumarate | Slight hygroscopicity |
| 9 | L-mandelate | Hygroscopicity |
| 10 | Sulfate | Slight hygroscopicity |
| 11 | Hydrobromate | Almost no hygroscopicity |
| 12 | Succinate | Slight hygroscopicity |
| 13 | Acetate | Strong hygroscopicity |
| 14 | P-toluenesulfonate | Slight hygroscopicity |
| 15 | L-malate | Almost no hygroscopicity |
| 16 | Maleate | Slight hygroscopicity |
| 17 | Methanesulfonate | Strong hygroscopicity |

EXAMPLE 18

(Z)—N-[2-(diethylamino)ethyl]-2-methyl-7-(1,2-dihydro-5-fluoro-2-oxo-3H-indol-3-ylidene)-4,5,6,7-tetrahydro-1H-indol-3-carboxamide (pharmaceutically active compound) and L-tartrate, L-malate, hydrochloride, phosphate, benzenesulfonate, maleate, fumarate, L-mandelate, sulfate, p-toluenesulfonate, lactate, citrate, hydrobromate, succinate, acetate and methanesulfonate salts thereof were measured for the solubility in water.

Testing Conditions:

Liquid chromatograph: Agilent 1200 HPLC system (diode array detector), ChemStation Column: Agilent $C_{18}$ 5µ 250×4.6 mm Mobile phase: acetonitrile/water Detection wavelength: 264 nm Flow rate: 1.0 ml/min Loading: 10 µl Testing Method About 100 mg sample to be tested was precisely weighed and placed into a 100 ml graduated flask at 25° C.; an appropriate amount of solvent [acetonitrile/water (80:20)] was added to dissolve the sample under ultrasonic sound, and the solution was diluted to a given scale and shaken up; 10 µl resulting solution was precisely measured and loaded into the liquid chromatograph, the chromatogram was recorded, and the peak area $S_{control}$ was measured.

10 ml purified water was measured and placed into a 25 ml Kjeldahl flask. The sample to be tested was gradually added at 25° C. until an insoluble solid appeared in the solution. The solution was treated under ultrasonic sound for 30 min and the insoluble solid was filtered off. 10 µl filtrate was precisely weighed and loaded into the liquid chromatograph, the chromatogram was recorded, and the peak area $S_{test}$ was measured.

$$\text{The solubility of the sample} = \frac{S_{test}}{S_{control}} \times 1 \text{ mg/ml}.$$

TABLE 2

Substance to Be Tested and Their Solubility in Water

| No. | Substance to Be Tested | Solubility in Water (mg/ml) |
|---|---|---|
| 1 | Pharmaceutically active compound | 0.0200 |
| 2 | Citrate | 38.1595 |
| 3 | Hydrochloride | 22.8000 |
| 4 | Phosphate | 29.7300 |
| 5 | L-tartrate | 10.6000 |
| 6 | Lactate | 24.0210 |
| 7 | Benzenesulfonate | 19.1925 |
| 8 | Fumarate | 0.0168 |
| 9 | L-mandelate | 14.7218 |
| 10 | Sulfate | 0.2361 |
| 11 | Hydrobromate | 3.5922 |
| 12 | Succinate | 13.3628 |
| 13 | Acetate | 30.6527 |
| 14 | P-toluenesulfonate | 0.4191 |
| 15 | L-malate | 38.6200 |
| 16 | Maleate | 1.3247 |
| 17 | Methanesulfonate | 12.2962 |

EXAMPLE 19

(Z)—N-[2-(diethylamino)ethyl]-2-methyl-7-(1,2-dihydro-5-fluoro-2-oxo-3H-indol-3-ylidene)-4,5,6,7-tetrahydro-1H-indol-3-carboxamide (pharmaceutically active compound) and L-malate, citrate, hydrochloride, phosphate and lactate salts thereof were measured for the plasma exposure (AUC) in animal body.

Testing Protocol:

Laboratory animal: male SD rats

Dosage: 10 mg/kg (based on pharmaceutically active compound)

Formulation for salts: dissolving in pure water

Formulation for pharmaceutically active compound: suspension in CMC (carboxymethylcellulose), 0.5%

Animal Grouping and Testing Course:

Each group includes three male rats having a weight of 180 to 210 g. Gavage administration was performed; the blood was collected at point of time: 5 min, 15 min, 30 min, 45 min, 1 h, 2 h, 4 h, 6 h, 10 h and 24 h; about 250 µl blood was collected from orbital venous plexus into a heparin-containing tube, centrifuged, and 100 µl plasma was used for LC-MS analysis.

Results of AUC Test:

TABLE 3

Samples to Be Tested and Their AUC

| Sample to Be Tested | AUC (0-t) (µg/L*h) |
|---|---|
| Pharmaceutically active compound | 127.9 |
| L-malate | 1489.4 |
| Hydrochloride | 184.9 |
| Citrate | 838.4 |
| Phosphate | 321.7 |
| Lactate | 651.8 |

EXAMPLE 20

Therapeutic effect of (Z)—N-[2-(diethylamino)ethyl]-2-methyl-7-(1,2-dihydro-5-fluoro-2-oxo-3H-indol-3-ylidene)-4,5,6,7-tetrahydro-1H-indol-3-carboxamide (pharmaceutically active compound) and L-malate salt thereof on human colon cancer HT-29 xenografts in nude mice.

Testing Protocol:
Laboratory animal: BALB/cA-nude mice, 6-7 weeks, ♀
Dosage: 40 mg/kg (based on pharmaceutically active compound)
Formulation for L-malate: dissolving in pure water
Formulation for pharmaceutically active compound: suspension in CMC (carboxymethylcellulose), 0.5%

Experimental Procedure:
Nude mice were subcutaneously inoculated with human colon cancer HT-29 cells. After the tumor grew to a size of 150 to 250 mm$^3$, the animals were randomly divided into three groups (d0). The animals were continuously administered through gavage for 21 days, and the tumor volume was measured 2 to 3 times per week. The tumor volume (V) was calculated according to the equation: $V=1/2 \times a \times b^2$, where a and b represent length and width respectively.

The relative proliferation of tumor=$T/C(\%)=(T-T_0)/(C-C_0) \times 100$, where T and C are the tumor volumes at the end of experiment, $T_0$ and $C_0$ are the tumor volumes at the start of experiment; the tumor inhibition rate=$1-T/C(\%)$.

Experimental Results:

TABLE 4

Certain Tested Compounds and Their Tumor Inhibition Rate

| Administration | Tumor Inhibition Rate (%) |
|---|---|
| Pharmaceutically active compound | 40 |
| L-malate | 54 |

All references cited in the description are hereby incorporated by reference in their entirety. While the disclosure has been described with respect to a limited number of embodiments, those skilled in the art, having benefit of this disclosure, will appreciate that other embodiments can be advised and achieved which do not depart from the scope of the description as disclosed herein.

The invention claimed is:

1. An acid addition salt of (Z)—N-[2-(diethylamino)ethyl]-2-methyl-7-(1,2-dihydro-5-fluoro-2-oxo-3H-indol-3-ylidene)-4,5,6,7-tetrahydro-1H-indol-3-carboxamide, wherein the salt comprises at least one of L-malate, citrate, hydrochloride, phosphate, or lactate salt of (Z)—N-[2-(diethylamino)ethyl]-2-methyl-7-(1,2-dihydro-5-fluoro-2-oxo-3H-indol-3-ylidene)-4,5,6,7-tetrahydro-1H-indol-3-carboxamide.

2. The salt of claim 1, wherein the salt comprises L-malate salt of (Z)—N-[2-(diethylamino)ethyl]-2-methyl-7-(1,2-dihydro-5-fluoro-2-oxo-3H-indol-3-ylidene)-4,5,6,7-tetrahydro-1H-indol-3-carboxamide.

3. The salt of claim 1, wherein the salt comprises citrate salt of (Z)—N-[2-(diethylamino)ethyl]-2-methyl-7-(1,2-dihydro-5-fluoro-2-oxo-3H-indol-3-ylidene)-4,5,6,7-tetrahydro-1H-indol-3-carboxamide.

4. The salt of claim 1, wherein the salt comprises hydrochloride salt of (Z)—N-[2-(diethylamino)ethyl]-2-methyl-7-(1,2-dihydro-5-fluoro-2-oxo-3H-indol-3-ylidene)-4,5,6,7-tetrahydro-1H-indol-3-carboxamide.

5. The salt of claim 1, wherein the salt comprises phosphate salt of (Z)—N-[2-(diethylamino)ethyl]-2-methyl-7-(1,2-dihydro-5-fluoro-2-oxo-3H-indol-3-ylidene)-4,5,6,7-tetrahydro-1H-indol-3-carboxamide.

6. The salt of claim 1, wherein the salt comprises lactate salt of (Z)—N-[2-(diethylamino)ethyl]-2-methyl-7-(1,2-dihydro-5-fluoro-2-oxo-3H-indol-3-ylidene)-4,5,6,7-tetrahydro-1H-indol-3-carboxamide.

7. A pharmaceutical composition, comprising the salt of claim 1 and a pharmaceutically acceptable carrier or excipient.

8. The pharmaceutical composition of claim 7, wherein the salt is the L-malate salt of (Z)—N-[2-(diethylamino)ethyl]-2-methyl-7-(1,2-dihydro-5-fluoro-2-oxo-3H-indol-3-ylidene)-4,5,6,7-tetrahydro-1H-indol-3-carboxamide.

9. A method of treating at least one of colon cancer, gastric cancer, lung cancer, leukemia, pancreatic cancer, bladder cancer, hepatocellular cancer, breast cancer, or ovarian cancer, comprising:
administering a therapeutically effective amount of an acid addition salt of (Z)—N-[2-(diethylamino)ethyl]-2-methyl-7-(1,2-dihydro-5-fluoro-2-oxo-3H-indol-3-ylidene)-4,5,6,7-tetrahydro-1H-indol-3-carboxamide to a subject in need thereof, wherein the salt comprises at least one of L-malate, citrate, hydrochloride, phosphate, or lactate salt of (Z)—N-[2-(diethylamino)ethyl]-2-methyl-7-(1,2-dihydro-5-fluoro-2-oxo-3H-indol-3-ylidene)-4,5,6,7-tetrahydro-1H-indol-3-carboxamide.

10. The method of claim 9, wherein the salt comprises L-malate salt of (Z)—N-[2-(diethylamino)ethyl]-2-methyl-7-(1,2-dihydro-5-fluoro-2-oxo-3H-indol-3-ylidene)-4,5,6,7-tetrahydro-1H-indol-3-carboxamide.

11. A composition, comprising at least two of L-malate, hydrochloride, phosphate, citrate, or lactate salts of (Z)—N-[2-(diethylamino)ethyl]-2-methyl-7-(1,2-dihydro-5-fluoro-2-oxo-3H-indol-3-ylidene)-4,5,6,7-tetrahydro-1H-indol-3-carboxamide.

12. The salt of claim 1, wherein the salt has a solubility of at least 0.2361 mg/ml in water, substantially improved plasma exposure, and substantially improved therapeutical effect as compared with (Z)—N-[2-(diethylamino)ethyl]-2-methyl-7-(1,2-dihydro-5-fluoro-2-oxo-3H-indol-3-ylidene)-4,5,6,7-tetrahydro-1H-indol-3-carboxamide.

13. The salt of claim 12, wherein the solubility is in a range of about 0.2361 to about 38.62 mg/ml, and wherein the salt has a plasma exposure (AUC) in a range of about 184.9 to about 1489.4 (μg/L*h).

14. The salt of claim 13, wherein the salt comprises L-malate and has a solubility of about 38.62 mg/ml and a plasma exposure (AUC) of about 1489.4 (μg/L*h).

15. The method of claim 9, wherein the method is for treating colon cancers, and wherein the therapeutically effective amount of an acid addition salt of (Z)—N-[2-(diethylamino)ethyl]-2-methyl-7-(1,2-dihydro-5-fluoro-2-oxo-3H-indol-3-ylidene)-4,5,6,7-tetrahydro-1H-indol-3-carboxamide has a solubility of at least 0.2361 mg/ml in water, substantially improved plasma exposure, and substantially improved therapeutical effect as compared with (Z)—N-[2-(diethylamino)ethyl]-2-methyl-7-(1,2-dihydro-5-fluoro-2-oxo-3H-indol-3-ylidene)-4,5,6,7-tetrahydro-1H-indol-3-carboxamide.

* * * * *